United States Patent [19]

Kino et al.

[11] Patent Number: 4,683,750
[45] Date of Patent: Aug. 4, 1987

[54] THERMAL ACOUSTIC PROBE

[75] Inventors: Gordon S. Kino, Stanford; Richard G. Stearns, Mountain View; Butrus T. Khuri-Yakub, Palo Alto, all of Calif.

[73] Assignee: The Board of Trustees of the Leland Stanford Junior University, Stanford, Calif.

[21] Appl. No.: 669,197

[22] Filed: Nov. 7, 1984

[51] Int. Cl.$^4$ ............................................. G01N 29/00
[52] U.S. Cl. ........................................ 73/606; 73/643
[58] Field of Search ................................... 73/606, 643

[56] References Cited

U.S. PATENT DOCUMENTS

4,012,951  3/1977  Kessler .................................. 73/606

Primary Examiner—Anthony V. Ciarlante
Attorney, Agent, or Firm—Flehr, Hohbach, Test, Albritton & Herbert

[57] ABSTRACT

A noncontacting method of measuring periodic surface heating is described. The perturbation of an externally generated acoustic wave is measured. The acoustic wave is generated in the air above a sample to be studied. The acoustic wave is directed onto the sample surface, coincident with a modulated light beam. Absorption of the light beam results in the periodic heating of the sample, at and near the sample surface. The air in contact with the sample surface is in turn heated, and produces a periodic phase shift in the reflected acoustic wave. This phase shift is detected and gives a direct measure of the periodic heating of the sample surface. An acoustic microscope may generate the acoustic wave. The sample is placed in water. An acoustic microscope lens produces an acoustic wave in the water, which focuses onto the sample surface, coincident with a modulated laser beam. The light beam is guided onto the sample using an optical fiber. Heating in the water directly above the illuminated sample produces a phase perturbation in the acoustic wave reflecting off the sample surface. This embodiment of the present invention allows surface heating to be measured with very high spatial resolution.

12 Claims, 13 Drawing Figures

THERMAL ACOUSTIC PROBE

This work was supported by Office of Naval Research Contract N0001478C0283.

The present invention is directed generally to a method and apparatus for measuring the surface and near-surface properties of material and more particularly, to measurements utilizing the perturbation of an acoustic wave propogating on or near the surface of the sample.

Non-destructive testing or analysis of material has assumed increasing importance in recent years. This includes examination of material properties, as well as the detection of cracks and flaws in materials. In many fields, such as the manufacturing and packaging of integrated circuits, conventional methods of non-destructive evaluation (e.g., acoustic and optical microscopy) are not always viable. Hence a growing need has developed for new techniques in the non-destructive evaluation of materials.

Therefore, it is an objective of the present invention to provide a novel and sensitive technique for the non-destructive evaluation of materials. The technique is based on the measurement of the phase perturbation of an acoustic wave, as it travels on or near the surface of a sample that is irradiated with intensity-modulated light. The acoustic wave is generated and received by external transducers. Such a measurement is capable of providing information concerning the optical, thermal, and for semiconductors, electronic properties of the sample under investigation.

A standard photoacoustic method for non-destructive testing is to use a laser beam incident on the surface of a sample to heat it. If the laser beam is chopped at a radian frequency $\omega$, the temperature of the sample is also modulated at the same radian frequency $\omega$, in the region where the lasser beam is incident, the temperature of the air above the sample varies at the same frequency $\omega$ as the temperature of the solid substrate. Because of this periodic temperature variation of the air, the air expands and contracts periodically, thus generating an acoustic wave. This acoustic wave can be detected with a microphone or acoustic sensor placed in an enclosure (an air cell) enclosing the heated region.

A similar technique has been used to detect the thermal expansion and contraction of the solid substrate itself. In this case an acoustic transducer is placed in contact with the opposite surface of the substrate being examined and detects the acoustic waves excited by the thermal modulation.

An acoustic wave, propagating through a region in which either the elastic constants or the mass density of a material are periodically perturbed will itself suffer a periodic phase perturbation. In the present invention, the periodic perturbation of the material properties results from the absorption of a modulated light beam. For example, in many semiconductors, it is known that the elastic constants vary with free-carrier density. Absorption of the modulated laser beam at the surface of a semiconductor results in the periodic photoinjection of free-carriers in a local region near the surface of the semiconductor. In the present invention, a surface acoustic wave propagating through this perturbed region suffers a periodic phase shift, which is found to be proportional to the photoinjected free-carrier density. The phase perturbation of the acoustic wave is detected as described below. It has been shown that by varying the modulation frequency of the incident light beam, information may be obtained concerning recombination times in the semiconductor.

It is therefore an objective of the present invention to provide a method and apparatus for the measurement of electronic properties of certain semiconductors (in particular, silicon). Furthermore, because the incident light beam may be focused and scanned across the surface of the semiconductor, the present invention provides a means of investigating such electronic properties with high spatial resolution.

Absorption of the modulated light beam at the surface of a sample also gives rise to periodic heating in the sample. Measurement of such heating may yield information concerning optical and thermal properties of the sample, as well as information on flaws or defects beneath the sample surface (several examples of this are given below). Associated with such periodic heating, there is, in general, found to be periodic changes in the mass density and elastic constants of all materials. Hence, the measurement technique described in the present invention is found to be a sensitive method of detecting periodic heating due to absorption of a modulated light beam.

In a second embodiment of the present invention, a noncontacting method of measuring periodic surface heating is described. Again, the perturbation of an externally-generated acoustic wave is measured. Here the acoustic wave is generated in the air above the sample to be studied. The acoustic wave is directed onto the sample surface, coincident with the modulated light beam. Absorption of the light beam results in periodic heating of the sample, at and near the sample surface. The air in contact with the sample surface is in turn heated, and produces a periodic phase shift in the reflected acoustic wave. This phase shift is detected as described below, and is found to give a direct measure of the periodic heating of the sample surface.

Because the acoustic wave propagates in the air above the sample, no mechanical contact with the sample is required. Hence, it is an objective of the present invention to provide a noncontacting method of measuring periodic temperature fluctuations at the surface of a material, with high sensitivity. As will be shown below, such a measurement can yield quantitative information concerning subsurface features of a sample, for instance, concerning the quality of bonding between a thin sample and its heat-sink backing.

A notable advantage of the present invention is the large flexibility inherent in its operation. Because the acoustic wave and light beam are externally generated, both may be varied at will. For example, the acoustic frequency may be varied independently of the modulation frequency of the light beam. This is very different from conventional photoacoustic measurements, in which the acoustic wave generated from the absorption of the modulated light beam is detected, and hence is constrained to be at the modulation frequency of the incident light.

Therefore, in the present invention, the modulation frequency of the incident light beam may be varied over a large range of values, independent of the acoustic frequency. As shown below, this allows useful information to be determined associated with thermal as well as electronic properties of materials.

Also, because the light and acoustic beams are independently generated, either or both of the beams may be focused or unfocused, depending on the nature of the measurement. By focusing both of the beams, information may be obtained with high spatial resolution. Using unfocused beams, one may determine thermal (or, for surface waves on semiconductors, electronic) properties of a sample, averaged over a larger spatial extent. Examples of both focused and unfocused configurations of the invention are discussed below.

A third embodiment of the present invention employs an acoustic microscope to generate the acoustic wave. In this embodiment, the sample is placed in water. An acoustic microscope lens produces an acoustic wave in the water, which focuses onto the sample surface, coincident with a modulated laser beam. The light beam may be guided onto the sample using an optical fiber. Just as in the case of air, heating in the water directly above the illuminated sample produces a phase perturbation in the acoustic wave reflecting off the sample surface. Because the focused acoustic beam is laterally very small in extent, this embodiment of the present invention allows surface heating to be measured with very high spatial resolution.

If the acoustic microscope is operated so that the focus of the acoustic beam is beneath the sample surface, a surface acoustic wave will, in general, be excited. Hence in this fashion the acoustic microscope may be used to generate surface acoustic waves on semiconductors, allowing measurement of the electronic properties of such semi-conductors, in the manner described above. This technique also makes it possible to measure the perturbation of surface acoustic waves by the temperature modulation of the material. Hence, in the present invention the use of an acoustic microscope in the generation of acoustic waves allows both measurement of the periodic heating at the surface of a sample, as well as measurement of electronic properties of some semiconductors. The use of the acoustic microscope, which can operate at very high frequencies, has the additional advantage that laser modulation frequencies varying from a few kilo hertz to several hundred megahertz can be employed.

In summary, in the present invention an acoustic wave, externally generated by an acoustic microscope, wedge, or air transducers, is perturbed due to the absorption of a laser beam or equivalent light source at the surface of a sample. The laser or acoustic beams may either be focused or unfocused, and the acoustic frequency, as well as the modulation frequency of the light beam may be independently varied over a wide range of values.

For a surface wave propagating on certain semiconductors (most notably, silicon), the acoustic phase perturbation will yield information concerning electronic properties of the semiconductor.

A non-contacting configuration of the present invention involving acoustic waves in air is able to measure periodic heating of the sample surface, with high sensitivity, over a large range of thermal modulation frequencies.

Modifications and improvements, as well as other advantages of the present invention will be clearly understood by reference to accompanying drawings wherein.

Figure 1A:
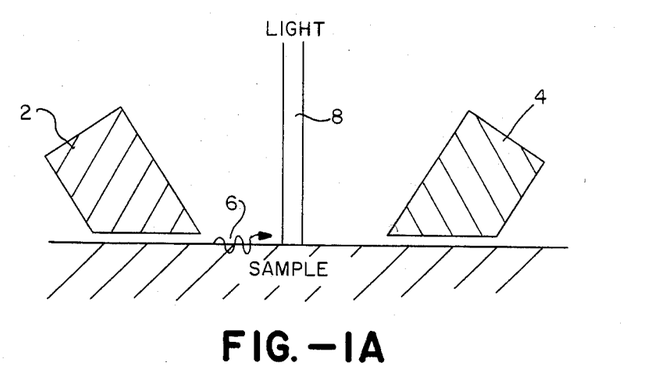
FIG. 1A represents a system of the type disclosed in the prior art.

FIG. 1A consists of an input surface wave transducer 2 and output surface wave transducer 4, each comprising a wedge type transducer. A modulated laser beam 8 generates carriers in a semiconductor material as well as heating the surface. The velocity of the surface acoustic wave passing along the material is changed in this region. Therefore, the acoustic wave 6 is used as a probe of the modulated generated carrier density in the material in the region where the laser beam generates carriers. By scanning the laser beam 8, (e.g., by moving the substrate) different parts of the material are probed and the technique can be used as a method of measuring electronic properties of the semiconductor material.

Figure 2:
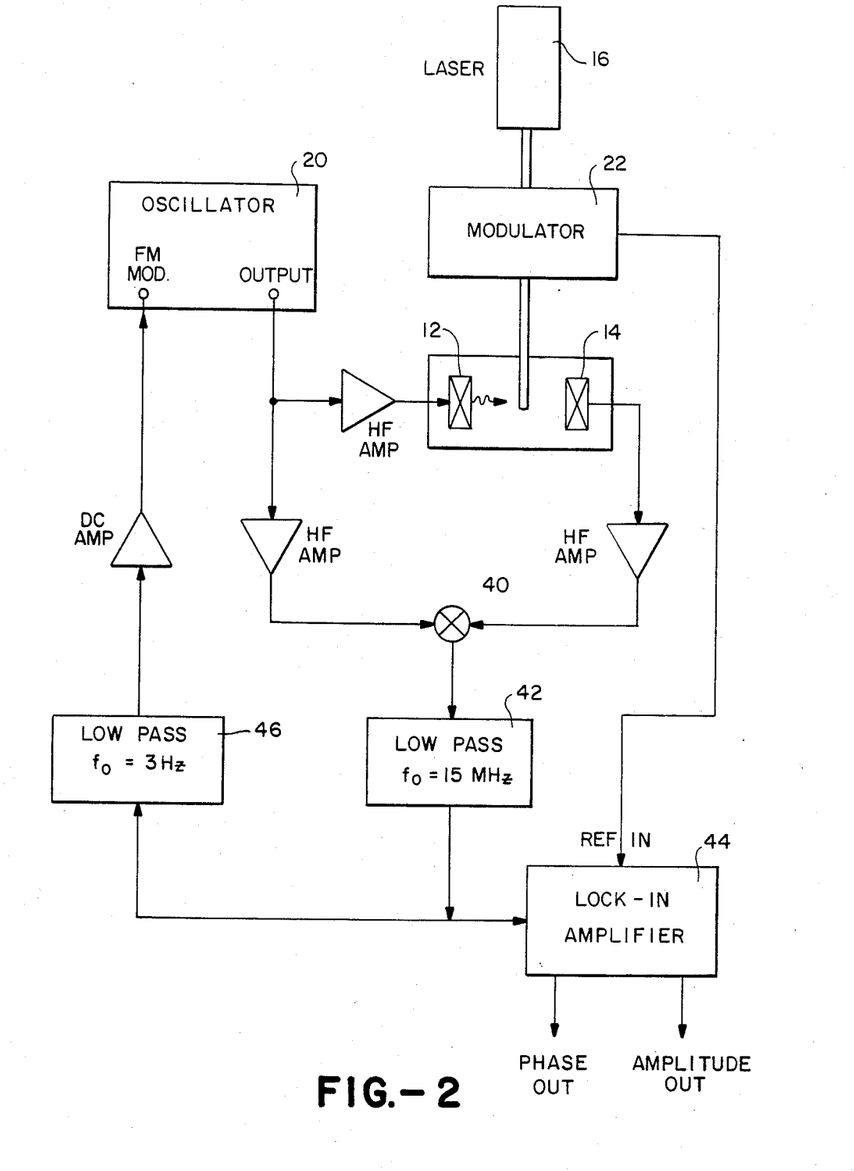
FIG. 2 is an illustrative schematic of the type of electronics necessary for analysis of the signal provided by the present invention.

An example of a detection scheme used to measure the changes in phase and magnitude of the acoustic wave is shown in FIG. 2.

Briefly, the output of the receiving transducer 14 is mixed at 40 with the output of the external oscillator 20. The oscillator frequency is adjusted to produce a $\pi/2$ phase shift between the two mixer input signals so the DC voltage level at the mixer output is zero. The mixer output, after low pass filtering 42, is directly proportional to the information sought from the periodic phase perturbation of the acoustic wave. This output signal is then fed into a two-phase lock-in amplifier 44 where both the magnitude and phase shift of the acoustic signal are recorded. A negative feedback system employing low pass filter 46 maintains the $\pi/2$ phase shift between the mixer input signals, keeping the measurement stable against long- term drift.

Figure 1B:
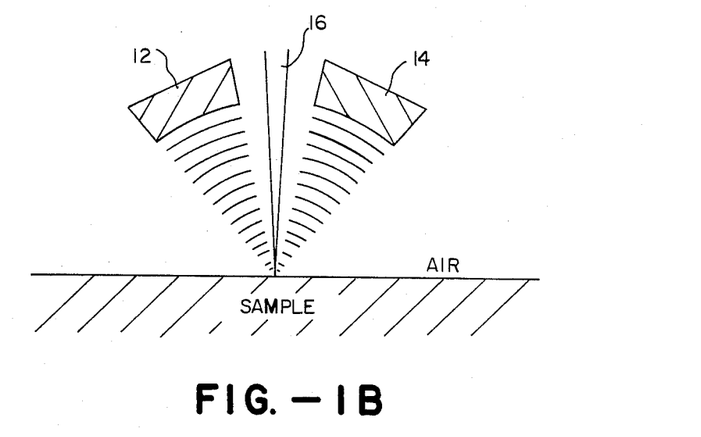
FIG. 1B schematically represents the system of the present invention and FIG. 1C illustrates the effects of using the present invention for analysis of a sample.
Figure 1C:
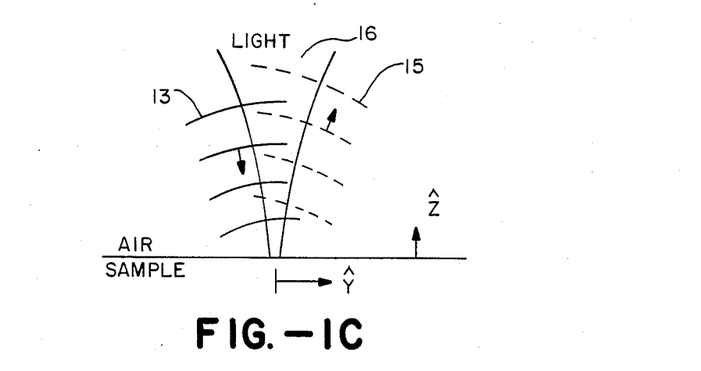

The method and apparatus described with respect to FIG. 1 may be especially useful in measuring periodic fluctuation in the free carrier density of silicon. This involves the measurement of the change in phase of an acoustic wave propagating through a region of modulating carrier density, the modulation being provided by the laser source 8. For example, the two surface wave transducers 2 and 4 are located adjacent the sample of silicon of interest. In FIG. 2, one transducer 12 is driven by the oscillator 20; the other transducer 14 receives the transmitted acoustic wave. An argon-ion laser beam, acousto-optically modulated, is directed onto the sample in the path of the acoustic wave. Absorption of the laser beam generates a modulated population of free carriers within the sample. The phase of the transmitted surface acoustic wave is perturbed at the modulation frequency of the laser beam and detected and analyzed using the electronics of FIG. 2. The results of this approach appear in FIGS. 5A and 5B, where both the magnitude and phase of the phase perturbation of the acoustic wave with respect to the modulation of the light beam are plotted as the function of the modulation frequency. The general shape of the curve is explained by the fact that at low modulation frequencies, the phase shift is dominated by periodic heating in the silicon.

Figure 5A:
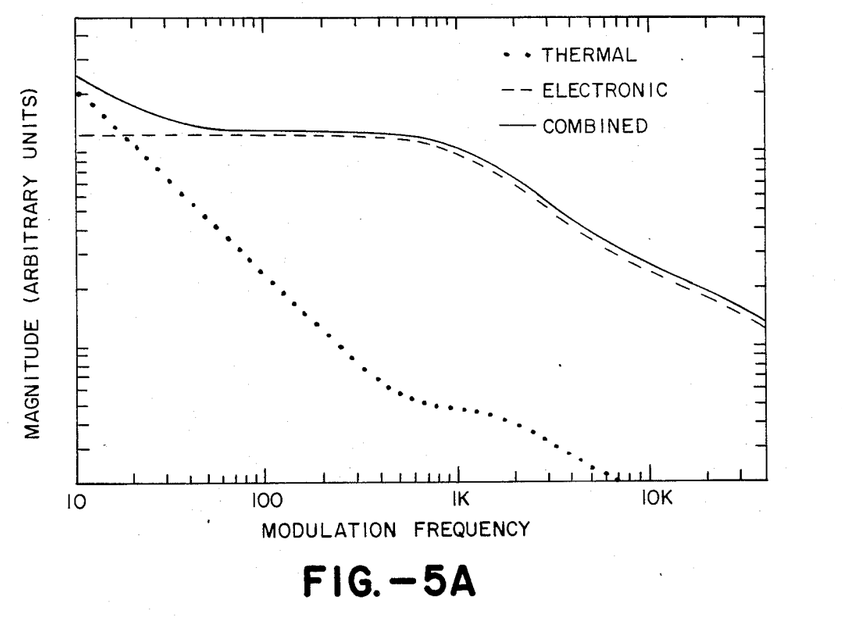
FIGS. 5a–b illustrates the effectiveness of the present invention in measuring electron generation and recombination in silicon.
Figure 5B:
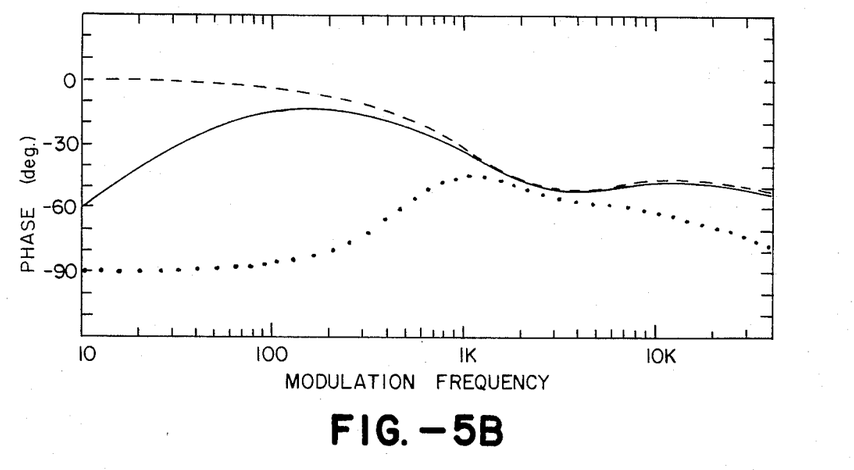

As the modulation frequency is increased, the periodic heating decays, but the density of the photogenerated free carriers remains unchanged. At intermediate modulation frequency, the acoustic phase perturbation is dominated by electronic effects. The magnitude of the acoustic perturbation plateau is at a level proportional to the density of free carriers generated, while the phase shift relative to the excitation approaches zero degrees. The electronic contribution only begins to decrease when the modulation frequency becomes comparable to the inverse lifetime of the generated carriers.

By measuring the frequency at which roll-off occurs, the free carrier lifetime can be determined. Thus, the rolloff and the magnitude of the phase shift at less than 1 kilohertz corresponds to the carrier lifetime of 155 microseconds. The inflection in both the magnitude and phase in phase at about 15 kilohertz appears to arise from low surface recombination velocities at the front and back surfaces of the silicon wafer.

Thus, useful information concerning both carrier lifetimes and surface recombination can be obtained from this novel method and apparatus for measurement. In this novel system, both the modulation frequency of the oscillator driving the transducer and the modulation frequency of the laser can be varied over wide ranges; therefore, this technique can be used to measure carrier lifetimes within a large range of values. Further, by modifying the focus of the laser beam, high spatial resolution can be achieved.

EXAMPLE

The sample was a wafer of n-type silicon, doped with $3 \times 10^{13}$ P atoms/cm$^3$. It was thermally oxidized to reduce surface recombination, and was previously found to have a bulk carrier lifetime of 153 usec. A laser beam 80 mW in time-averaged power was used. The acoustic wave was a Rayleigh type surface wave, launched and received at 50 MHz by a pair of wedge transducers.

To obtain quantitative information from such experimental results, a theory has been developed to predict the phase perturbation of the acoustic wave propagating through the illuminated region of the silicon. The acoustic perturbation can be shown to be of the form:

$$\Delta\phi = (W/4) \int_V [-\Delta\rho V_i V_i^* + S_{ij} \Delta C_{ijkl} S_{kl}^*] dV \qquad (1)$$

here
$\Delta\rho$ and $\Delta C_{ijkl}$ are the change in mass density and elastic constant in the silicon, $S_{ij}$ and $v_i$ are the strain and particle velocity due to the surface acoustic wave, V is the volume of the perturbed region, and P is the total acoustic beam power. It is assumed in equation (1) that the changes in density and elastic constant act as a weak perturbation on the acoustic wave.

To compare the theory to experiment, it is necessary to evaluate the integral in equation (1). To do so, we solve first for the periodic temperature and free-carrier concentrations within the sample. A simple analysis shows that in the experiment the magnitude of the periodic free-carrier density was approximately $10^{16}$ cm$^{-3}$. Hence, it is clear that ambipolar diffusion must be assumed for the generated free carriers. The diffusion in all cases is taken to be one-dimensional, which is reasonable considering the size of the laser beam and the width of the acoustic beam (7 mm) used in the experiment. For both the thermal and electronic diffusion it is necessary to take into account the finite thickness of the sample (330 μm). For the carrier diffusion, it is assumed that no traps are present, and that at each point within the sample the excess electron and hole densities are equal.

In solving for the electronic and thermal diffusion, physical parameters corresponding to the experiment are used. We take the ambipolar diffusion coefficient to be 14.6 cm$^2$/sec., the bulk free-carrier lifetime to be 155 μsec, and the front and back surface recombination velocities to be 15 cm/sec and 30 cm/sec, respectively. We assume a thermal diffusitivy of 0.88 cm$^2$/sec for the silicon, and a thermal conductivity of 1.45 W/cm-K.

To determine $\Delta\rho$ and $\Delta C_{ijkl}$ in equation (1), it is necessary to know the dependence of the mass density and elastic constants on both the temperature and free-carrier concentration. The change in the elastic constants with temperature is taken to be: $dc/dT = -1.4 \times 10^7 N/m^2 - K$, $dc_{12}/dT = -5.8 \times 10^6 N/m^2 - K$, and $dc_{44}/dT^{11} = 6.2 \times 10^6 N/m^2 - K$. The dependence of the mass density on temperature is: $d/dT = -2.1 \times 10^{-2}$ kg/m$^3 - K$. In the non-degenerate regime, it is found that the elastic constants vary linearly with the free-electron density. The dependence of the elastic constants on the free-electron density may be written as: $dc_{11}/dn = -1.6 \times 10^{-10}$ N-cm$^3$/m$^2$, $dc_{12}/dn = 7.7 \times 10^{-11}$ N-cm$^3$/m$^2$, and $dc_{44} = -3.0 \times 10^{-11}$ N-cm$^3$/m$^2$. The effect of free holes on the elastic constants is not as well known, and we assume the values: $dc_{11}/dp = 2.2 \times 10^{-11}$ N-cm$^3$/m$^2$, $dc_{12}/dp1.1 \times 10^{-11}$ N-cm$^3$/m$^2$, and $dc_{44}/dp = -3.2 \times 10$ N-cm$^3$/m$^2$, for the dependence of the elastic constants on the free-hole density.

The integral in equation (1) has been evaluated, using for the acoustic fields those corresponding to the experiment: a 50 MHz Rayleigh wave propagating along the [100] direction of a (001)-cut silicon wafer. Comparison of the experimental results with the theoretical prediction provides excellent agreement. The roll-off in the magnitude of the phase perturbation at 1 KHz corresponds to the bulk carrier lifetime of 155 usec.

The inflection in both the magnitude and phase at ~15 KHz appears to arise from the low surface recombination velocity at back surfaces of the silicon wafer. FIG. 5(b) shows the theoretical contribution to the phase perturbation from the thermal and electronic effects separately. Note that the thermal contribution has become negligable at a modulation frequency of approximately 100 Hz.

From the above results it appears that we have a quantitative understanding of the technique, and that useful information concerning bulk carrier lifetimes as well as perhaps surface recombination, may be obtained from this novel measurement. Because of the wide range of modulation frequencies available, it should be possible with this technique to measure bulk carrier lifetimes within a large range of values—from perhaps 0.1 μsec to 1 msec. It should also be possible to focus the incident laser beam, and hence obtain information with high spatial resolution.

An interesting characteristic of the Rayleigh surface wave is that it decays exponentially into the bulk of the sample. This decay length varies inversely with the frequency of the acoustic wave: at 50 MHz it is approximately 30 μm. One might envision using higher frequency surface waves, and varying the frequency to obtain information concerning generated carrier densities within the depth of the sample.

The technique should be applicable to most multivalley semiconductors, and to any other semiconductors that exhibit an electronic contribution to the elastic constants. It should be sensitive to any method of periodic carrier injection.

The method and apparatus of FIG. 1B involves exciting an acoustic wave in the outside medium, typically air, reflecting off the surface of the sample under inspection and bringing it back to a second transducer 14. A laser beam 16 is used to heat the sample in the region of interest. If the temperature of the air varies, perturbation of the acoustic wave by the temperature variation can be used to measure the surface temperature of the substrate.

This technique has proven to be a powerful non-contacting method for measuring the surface temperature fluctuations of materials. It has the advantage of being able to probe a relatively small region, the size of the region being fixed by the laser spot size 16. As disclosed above, the modulation frequency of both the oscillator 20 (FIG. 2) driving the transducer 12 or the chopper modulator 22 (FIG. 2) driving the laser focused on the sample can be varied, providing an extremely large thermal modulation frequency bandwidth within the system.

The details of this form of sample inspection are shown in FIG. 1C, wherein the output of transducer 12 is indicated at 13 and reflections from the surface sample to the transducer 14 are indicated by the dotted lines 15. The impinging light from the laser itself is indicated at 16.

The phase of the acoustic wave is perturbed by heating in the air above the sample, and it is this phase perturbation that is measured. We assume no direct absorption of the light in the air itself, and therefore all heating arises from absorption of the light in the sample.

The general expression for the phase perturbation of an acoustic wave propagating through a region of local periodic heating has been discussed in previous publications. For acoustic waves in air, the phase perturbation can be evaluated directly. In doing so, we assume, for simplicity, that the focused acoustic wave and laser beam both have Gaussian power distributions: $\exp(-r^2/a^2)$ and $\exp(-r^2/R^2)$, respectively where a is the radius of the accoustic beam, and R the radius of the focused laser beam. We also assume plane acoustic waves in the volume of air within a few thermal diffusion lengths of the sample. With these simplifications, it is found that for an ideal gas, the acoustic phase perturbation can be written as:

$$\Delta\phi = e^{i\Omega} \frac{t(1-\xi)}{2\pi} \frac{\omega_0}{v_g} I_0 \pi R^2 \frac{\beta^1}{V} \frac{dV}{dT}$$

$$\int_0^\infty \lambda \frac{\exp[-(R^2+a^2)\lambda^2/4]}{b_g(k_s b_s + k_g b_g)(b_s + \beta)} d\lambda$$

Here $\Omega$ is the angular modulation frequency of the incident laser beam, $\beta$ is the optical absorption coefficient of the sample, $k_i$ and $\mu_i$ are the thermal conductivity and diffusion length, respectively in the medium i (i=g for gas, i=s for sample), and $b_i$ is the principal root of the radical $(\lambda^2+2i/\mu_i^2)^{\frac{1}{2}}$. $\omega_0$ is the angular frequency of the acoustic wave, $v_g$ is the velocity of sound in the gas, $(1/V)(dV/dT)$ is the relative change in volume with temperature in the gas, and $\xi$ is the ratio of the specific heat at constant pressure to that at constant volume in the gas. In the unfocused configuration, the phase perturbation of the acoustic wave takes on the limiting form of Eq. (1) for large R and a.

Periodic phase shifts in the acoustic wave of $5 \times 10^{-5}$ degrees have been measured using this approach. This corresponds to temperature fluctuations in the order of $10^{-3\circ}$ C. at the surface of the sample. A particularly interesting aspect of the measurement technique is the large range of modulation frequencies obtainable. We have measured signals at frequencies of a few hertz to several tens of kilohertz.

EXAMPLE OF FOCUSED CONFIGURATION

In the focused configuration, a spherical acoustic transducer, designed for use in air, was driven at 2.0MHz with the acoustic wave focusing to a diameter of 320 µm on the sample surface. A laser beam, with a time averaged power of 50 mW, was focused to a diameter of approximately 50 µm at the sample surface.

Figure 3A:
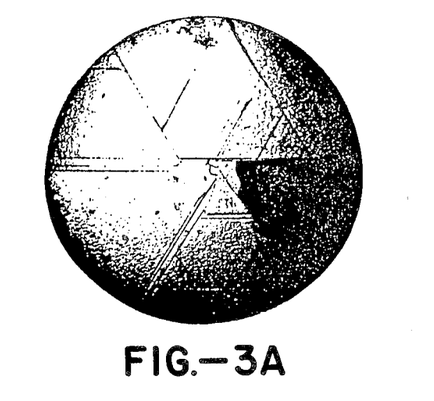
FIGS. 3a–c includes acoustic microscope images of the bonding between a silicon substrate and an aluminum backing, the images being generated using the present invention as shown in FIG. 6.
Figure 3B:
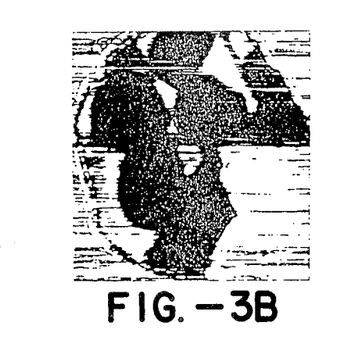
Figure 3C:
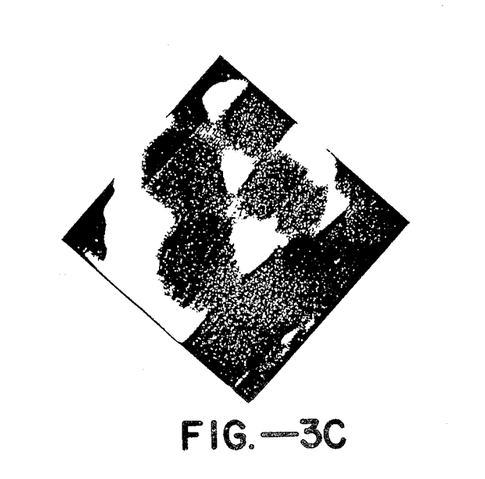

To investigate the application of this configuration to thermal imaging, we indium-bonded an 80 µm thick wafer of silicon onto a thick block of aluminum. FIG. 3a shows an optical image of the wafer. A section of the wafer has been detached from the aluminum block, and several cracks are visible on the silicon surface. The circular wafer is approximately 1 cm in diameter. FIG. 3b is an acoustic microscope (50MHz) image of the bonded wafer having dark areas corresponding to regions where the acoustic wave is transmitted through the bond into the aluminum backing, and hence, correspond to regions of good bonding. Bright regions in the image correspond to areas of disbonding. The bonded wafer was then scanned under the coincident light and acoustic beams, and the acoustic phase perturbation monitored as shown in FIG. 3c. Again, the dark regions in the image correspond to areas of less heating at the surface of the silicon. This indicates good bonding, where the heat is able to flow into the aluminum backing. The bright regions correspond to higher surface temperatures, and to areas of disbonding. There is good agreement between the acoustic and thermal images.

Figure 4A:
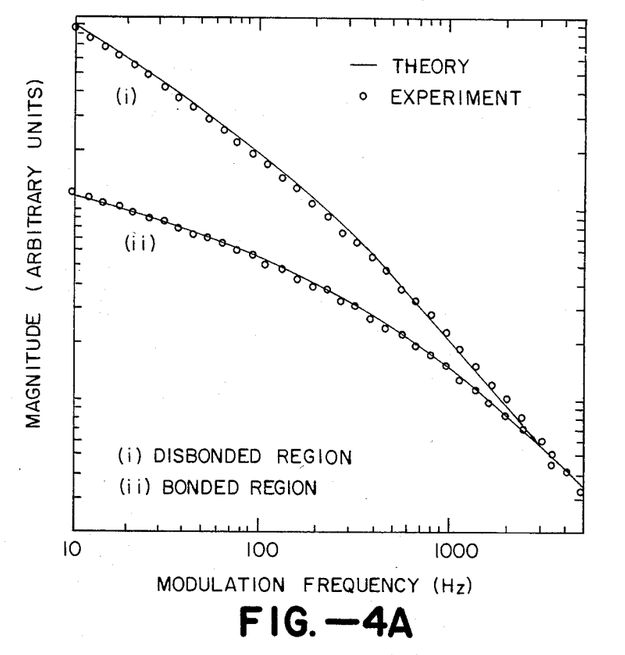
FIGS. 4a–c comprises graphs illustrating the utility of the present invention in testing effectiveness of bonding.

FIG. 4a shows the dependence of the magnitude of the acoustic phase perturbation on the modulation frequency of the laser beam in the bonded and disbonded regions. Also shown are theoretical curves, extending the theory of Eq. (1) to apply to a bonded wafer. For the disbonded region, we assume the silicon wafer to be air backed. In the bonded region we assume the bond to be perfect thermal match between the silicon and the aluminum. It is seen that the theoretical curves fit the data well, giving quantitative support to our interpretation of the thermal image.

EXAMPLE OF UNFOCUSED CONFIGURATION

An extension of the above results would be to thermally image the bonding of a silicon die in a commercial package. The typical thickness of a silicon die is approximately 330 µm. It is well known that the resolution of thermal imaging is severly degraded the deeper beneath the surface the feature to be imaged exists. For a silicon die 330 µm thick, it becomes virtually impossible to thermally image an underlying bond with sufficient resolution to see the important features of that bond. An alternative approach is to measure the average thermal properties of the bond, using the unfocused configuration.

This approach was followed in the study of the bonding of several silicon dies, in a standard power transistor (To-3 case) package. In this configuration, the die, approximately 4mm × 4mm in area, was centered in the path of an unfocused acoustic beam approximately 6mm in diameter. An unfocused, modulated laser beam (~2mm in diameter) was directed onto the die, heating a large portion of the die surface. In such a configuration, the heating can be considered to be one dimensional. Because a large portion of the die is now heated, the resulting phase perturbation will reflect the thermal properties of the bond, averaged over most of the bond area.

By measuring the dependence of the acoustic phase perturbation on the modulation frequency of the incident laser beam, one may extract information concerning the thermal properties of the bond. In our experiments, measurements are normalized to the case of a completely disbonded die. At high modulation frequencies, the phase and magnitude of the acoustic phase perturbation approach a single value for two different bonds. This is to be expected, since at a high modulation frequency the thermal wave in the silicon is damped out before it is able to reach the bond and reflect back to the silicon surface. At low modulation frequencies, the surface temperature of the silicon will be strongly affected by the thermal properties of the bond. Hence a poor bond, which does not allow heat to flow easily into the transistor case, will give rise to a larger acoustic phase perturbation at low modulation frequencies.

To make this result more quantitative, the data can be compared with the data of our theoretical expression for the acoustic phase perturbation, extending the theory to apply to the heating of a wafer bonded to a backing of finite thickness. As in the experimental data, theoretical predictions are normalized to the predicted acoustic phase perturbation of a disbonded silicon die. In evaluating the theory, the most important parameter governing the modulation frequency dependence of the phase perturbation is the ratio of the thermal conductivity of the bond to the bond thickness. The experimental data from all of the bonds fits our theory by the adjustment of this single parameter. For all of the bonds studied, take the silicon die to be 330 $\mu$m in thickness, to have a thermal conductivity of 1.4W/cm-K, and a thermal diffusion length of $1.33/\sqrt{\Omega \text{cm}}$.

The transistor case to which the die is bonded is aluminum, 3mm in thickness, with a thermal conductivity of 2.5W/cm-K and a thermal diffusion length of $1.39/\sqrt{\Omega \text{cm}}$.

Figure 4B:
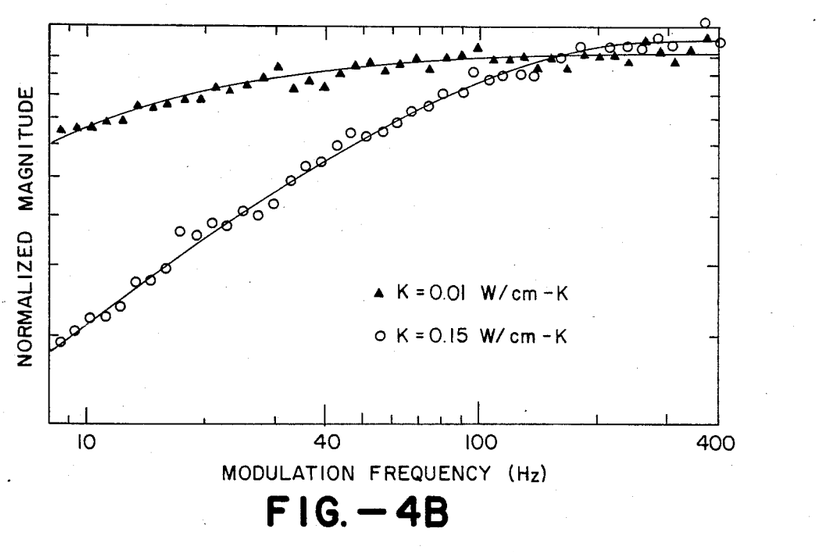
Figure 4C:
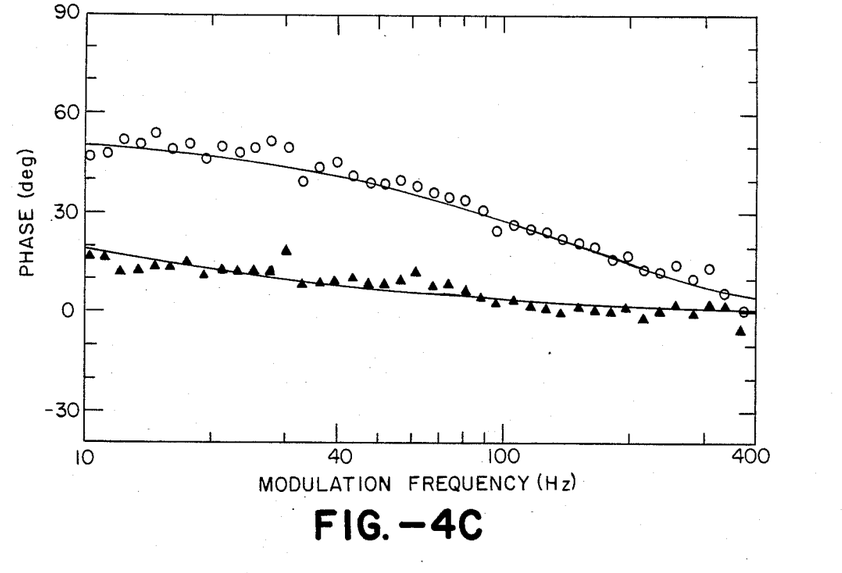

FIG. 4B and 4C show the fit of the theoretical model to the experimental data. The agreement is seen to be very good. Assume that the average thermal diffusion length in the bond itself is $1.0/\sqrt{\Omega \text{cm}}$, although the fit to the data does not appear to depend strongly on this parameter. Assuming an average bond thickness of 30 $\mu$m for both bonds, the average thermal conductivity of the bonds is 0.01W/cm-k, and 0.15W/cm-k, a more than ten-fold difference between the two bonds. These two numbers represent the worst and best bonds tested, respectively. From the results it appears that quantitative information concerning the thermal properties of the bonds may be available.

In summary, successful imaging of a bond between a thin wafer of silicon and aluminum backing is possible. In the unfocused configuration, the average thermal properties of bonds in commercially packaged dies can be measured. By fitting experimental data to theory, quantitative information concerning the bonds is extracted. This technique is inherently quite fast, and may yield a quick measure of the average bond properties.

Figure 6:
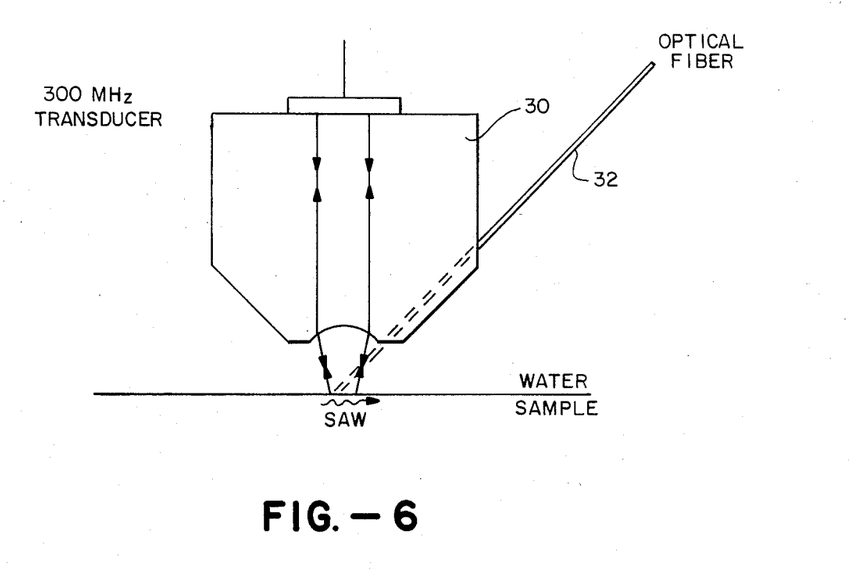
FIG. 6 is a schematic of an alternative embodiment of the present invention utilizing an acoustic microscope.

An alternative embodiment is shown in FIG. 6 in which the technique described with reference to Figure 1B is incorporated to work with an acoustic transducer 30 of the type already well known in the art. An optical fiber 32 is used to guide the light into the focal region of the acoustic microscope. If the beam is focused on the surface of the substrate, variations in temperature in the water medium can be detected by the acoustic microscope and therefore, provide a direct measurement of surface temperature.

The advantage of the system is that the acoustic microscope can be used to excite the desired region, and can confine the response to a small region. Therefore, the acoustic microscope can be operated in this mode to obtain quantitative data on properties associated with thermal effects or carrier generation effects.

It is believed such carrier generation effects can be extrapolated to give data on density and thickness of doping layers, information which is especially important in production of semiconductor devices.

Other modifications and improvements of the present invention may be realized by a person of skill in the art who has studied the present invention disclosure. Therefore, the subject invention is to be limited only by the scope of the following claims.

What is claimed:

1. A method of measuring surface effects of a substrate comprising propagating an acoustic wave in a medium over the surface of the substrate, heating said substrate by impinging a modulated incident beam of radiation on the substrate, measuring the change in phase of the propagated wave in response to this impinging beam of radiation and resulting heating of the substrate as it affects said medium to measure the surface temperature of the substrate.

2. A method of measuring surface temperature of a substrate as claimed in claim 1 comprising the further step of moving the incident beam of light relative to the surface of the substrate.

3. A method of measurement as claimed in claim 2 wherein said scanning step is carried out by moving the substrate.

4. A method as claimed in claim 1 wherein said medium comprises air.

5. A method of measurement as claimed in claim 1 wherein said means for propagating an acoustic wave comprises an acoustic microscope, and said medium comprises water.

6. A method as in claim 5 wherein the incident beam of radiation is a beam of light and comprising the step of varying the modulation frequency of the incident beam of light while maintaining tthe acoustic frequency output of the acoustic microscope substantially constant.

7. A method as claimed in claim 5 comprising the steps of modifying the output of the acoustic microscope to modify the area of interest under inspection.

8. A method as in claim 1 wherein the incident beam of radiation is a beam of light and including the step of modifying the heating effects by adjusting the modulation of frequency of the incident beam of light.

9. A method as claimed in claim 1 for measuring electronic properties of silicon, wherein the step of impinging an incident beam of radiation on the substrate comprises modulating the carrier density in the substrate, and said measuring step comprises measuring the perturbation in phase of the wave as it propagates over the region of modulated carrier density.

10. A method as claimed in claim 1 wherein the step of propagating an acoustic wave comprises driving a transducer with an oscillator, and the step of measuring the change in phase comprises detecting the propagation wave, mixing the oscillator output signal and the detected wave, adjusting the oscillator output to produce a $\pi/2$ phase shift between the two mixer input signals, the mixer output being proportional to the periodic phase perturbation of the acoustic wave.

11. A method as claimed in claim 10 including the step of lowpass filtering the mixer output, the output of the lowpass filter being proportional to perturbation of the modulated light signal.

12. A method as claimed in claim 1 wherein the radiation source comprises a laser.

* * * * *